(12) United States Patent
Mabe

(10) Patent No.: US 11,017,519 B2
(45) Date of Patent: May 25, 2021

(54) FLUID MONITORING SYSTEM

(71) Applicant: Atten2 Advanced Monitoring Technologies S.L., Eibar (ES)

(72) Inventor: Jon Mabe, Eibar (ES)

(73) Assignee: Atten2 Advanced Monitoring Technologies S.L., Eibar (ES)

( * ) Notice: Subject to any disclaimer, the term of this patent is extended or adjusted under 35 U.S.C. 154(b) by 125 days.

(21) Appl. No.: 15/496,430

(22) Filed: Apr. 25, 2017

(65) Prior Publication Data
US 2017/0309012 A1   Oct. 26, 2017

(30) Foreign Application Priority Data

Apr. 26, 2016   (EP) .................................... 16382179

(51) Int. Cl.
*G06T 7/00*   (2017.01)
*G01N 15/06*   (2006.01)
(Continued)

(52) U.S. Cl.
CPC ........... *G06T 7/0004* (2013.01); *G01N 15/06* (2013.01); *G01N 21/8806* (2013.01);
(Continued)

(58) Field of Classification Search
CPC .......... G01N 21/00; G01N 2015/0011; G01N 2015/0053; G01N 33/2888; G01N 21/85;
(Continued)

(56) References Cited

U.S. PATENT DOCUMENTS

| 5,572,320 A | 11/1996 | Reintjes et al. |
| 5,790,246 A * | 8/1998 | Kuhnell ............. G01N 15/0656 250/301 |

(Continued)

FOREIGN PATENT DOCUMENTS

| EP | 0711999 | 5/1996 |
| EP | 2980557 | 2/2016 |

(Continued)

OTHER PUBLICATIONS

Extended European Search Report dated Oct. 21, 2016 for European Application 16382179.6 filed Apr. 26, 2016.
(Continued)

*Primary Examiner* — Daniel Chang
(74) *Attorney, Agent, or Firm* — Andrus Intellectual Property Law, LLP (57) ABSTRACT

A sensor system for inspecting oil, which comprises a micromechanical cell defining a cavity for allowing the entrance/outcome of oil within/from said cavity through respective inlet and outlet. Inside said micromechanical cell there are: first and second transparent protective means; a light source configured to emit incoherent light towards said oil; an opaque plate disposed between said light source and said first transparent protective means, having a pin-hole configured to permit the passage of illumination towards said oil, said pin-hole being located at a first distance from a focussing plane defined by said oil in cavity; an image sensor to capture images of the oil disposed within said cavity located at a second distance from said focussing plane defined by said oil in cavity.

14 Claims, 10 Drawing Sheets

(51) Int. Cl.
  *G01N 21/88* (2006.01)
  *G01N 33/28* (2006.01)
  *G02B 5/00* (2006.01)
  *G02B 5/02* (2006.01)
  *H04N 5/335* (2011.01)
  *G01N 15/00* (2006.01)
  *G02B 21/00* (2006.01)
  *H04N 5/225* (2006.01)

(52) U.S. Cl.
  CPC ......... *G01N 33/2888* (2013.01); *G02B 5/005* (2013.01); *G02B 5/0278* (2013.01); *H04N 5/335* (2013.01); *G01N 33/2858* (2013.01); *G01N 2015/0011* (2013.01); *G01N 2015/0053* (2013.01); *G01N 2015/0693* (2013.01); *G01N 2201/062* (2013.01); *G02B 21/0008* (2013.01); *G02B 21/0016* (2013.01); *G06T 2207/10016* (2013.01); *G06T 2207/30164* (2013.01); *H04N 5/2256* (2013.01)

(58) Field of Classification Search
  CPC ........... G01N 15/06; G01N 2015/0693; G01N 21/534; G06T 2207/10016; G06T 2207/30164; G06T 7/0004
  USPC .......... 348/781, 92, 84; 73/293; 356/70, 338
  See application file for complete search history.

(56) References Cited

U.S. PATENT DOCUMENTS

| | | | | |
|---|---|---|---|---|
| 5,859,705 | A * | 1/1999 | Benedetto | G01N 15/0205 356/336 |
| 7,385,694 | B2 | 6/2008 | Kolp et al. | |
| 2003/0038940 | A1* | 2/2003 | Metcalfe | G01N 21/538 356/437 |
| 2004/0100636 | A1* | 5/2004 | Somekh | G01N 21/6458 356/497 |
| 2004/0165274 | A1* | 8/2004 | He | G02B 5/0221 359/599 |
| 2008/0231808 | A1* | 9/2008 | Van de Velde | A61B 3/1025 351/221 |
| 2010/0309457 | A1* | 12/2010 | Cui | G02B 21/0004 356/121 |
| 2011/0096157 | A1* | 4/2011 | Fine | G02B 21/0008 348/79 |
| 2011/0170105 | A1* | 7/2011 | Cui | G02B 21/33 356/450 |
| 2011/0234757 | A1* | 9/2011 | Zheng | G01N 15/147 348/46 |
| 2012/0061587 | A1* | 3/2012 | Wu | G01N 21/6458 250/459.1 |
| 2012/0098950 | A1* | 4/2012 | Zheng | G02B 21/06 348/79 |
| 2012/0250027 | A1* | 10/2012 | Zheng | B82Y 20/00 356/491 |
| 2013/0258091 | A1* | 10/2013 | Ozcan | G06K 9/0014 348/79 |
| 2013/0280752 | A1* | 10/2013 | Ozcan | G01B 9/02047 435/29 |
| 2013/0323757 | A1* | 12/2013 | Poher | G01N 15/1463 435/7.25 |
| 2014/0009621 | A1* | 1/2014 | Tucker | G01N 15/0227 348/159 |
| 2014/0248656 | A1* | 9/2014 | Demirci | G01N 33/5029 435/30 |
| 2015/0204773 | A1 | 7/2015 | Ozcan et al. | |

FOREIGN PATENT DOCUMENTS

| | | |
|---|---|---|
| EP | 16382179.6 | 4/2016 |
| WO | WO 1997/040360 | 10/1997 |
| WO | WO 2012/094523 | 7/2012 |
| WO | WO 2014/154915 | 10/2014 |
| WO | WO-2014154915 A1 * | 10/2014 ......... G01N 15/0227 |

OTHER PUBLICATIONS

Kim, Sang Bok. et al., "Lens-Free Imaging for Biological Applications," J Laboratory Automation, 17(1), Jan. 27, 2012, pp. 43-49.

Lee, Hun et al., "Various On-Chip Sensors with Microfluidics for Biological Applications," Sensors, 14(9), Sep. 12, 2014, pp. 17008-17036.

\* cited by examiner

FLUID MONITORING SYSTEM

CROSS-REFERENCE TO RELATED APPLICATIONS

This patent application claims the benefit of priority of European Patent Application No. 16382179.6, filed Apr. 26, 2016,which is incorporated herein by reference in its entirety.

TECHNICAL FIELD

The present invention relates to the field of fluid monitoring for determining the general condition of fluids from the point of view of their degradation and particle content. More specifically, it relates to the field of oil monitoring, in particular lubricating oils, in order to obtain their state of degradation and to obtain information on the machinery lubricated by those oils on the basis of their particle content.

BACKGROUND OF THE INVENTION

Lubricating oil is one of the key components in many industrial machines and provides a lot of information regarding the machine's condition. Oil heating, for example, can be a sign that the machine is not operating in optimum conditions, and the presence of particles in the oil may indicate a future failure or considerable wear in the lubricated components. It could even point to the existence of cracks or faults in joints that could allow the entry of external contaminants. Some of the parameters that are interesting to monitor in lubricating oil are as follows: particle determination (for example, quantification, classification of size or determination of shape), bubble content in the system or oil degradation based on colour.

In order to prevent shutdowns and failures in industrial machinery due to lubrication-related reasons, different techniques are currently used. Some of these techniques are 'off-line' measurement methodologies (oil sample analysis in the laboratory). However, they do often not provide a sufficiently early detection of the degradation process due to the low frequency with which these measurements are usually taken. Furthermore, in many contexts (transport, industrial, power . . . ) this control methodology entails a significant logistical and financial burden.

To deal with this drawback, alternative technologies based on sensors have been developed for analysing the machine's condition in real time. Among these detectors, those based on image analysis are remarkable. As a matter of example, U.S. Pat. No. 5,572,320 describes an image analysis detector that includes a lighting system based on a pulsed laser. Detection is carried out by means of a planar array of light sensitive photodiodes or phototransistors. However, this system is not capable of discriminating between particle shapes. Also, its measuring cell consists of a moving part that positions the oil in a specific place, and this complicates development and can be an important source of errors.

In turn, patent U.S. Pat. No. 7,385,694B2 describes a detector through image analysis that includes a lighting system based on a pulsed laser and a camera for gathering images of the oil subjected to such lighting. However, the device of this patent does not allow a homogenous lighting to be provided over an inspection area that is greater than the beam of light itself. Also, the device requires a pump in order to pump the fluid to the measuring zone.

International patent application WO97/40360 discloses an apparatus based on an optical sensor for determining contamination on machine wear by measuring wear particles in a fluid used in the machine.

Also, international patent application WO2014/154915A1 discloses a system for inspecting oil based on a lighting system, an image capture system and a lens disposed between the image capture system and the oil flow.

The above mentioned disclosures are based on complex systems requiring many components; they are bulky and difficult to deploy in target applications in industrial environments. Taking into account that they need to be submerged in oil and installed in the field, the risk of failure is high, which implies maintenance work and cost and potential failure in the machine under supervision. Additionally, the moving parts require a semi-static sample in order to obtain a proper image, which is not compatible with a running sample.

On the other hand, a lens-free imaging technology has been reported for biological applications, for example by Sang Bok Kim et al. (Lens-Free Imaging for Biological Applications, Journal of Laboratory Automation, 17(1) 43-49, ©2012 Society for Laboratory). Lens-free imaging is based on a light source that illuminates an object through a pin-hole or aperture and an image sensor located at the other side of the object. The object is correctly focused thanks to diffraction effects generated at the pin-hole when hit by the coherent, incoherent or partially coherent light. A focusing lens is therefore not required. This technology has been proved to have remarkable biomedical applications in microscopy, for example in portable diagnostic systems.

As a matter of example, international patent application WO2012/094523A2 discloses a system for three dimensional imaging of an organelle contained within a sample that includes an image sensor, a sample holder adjacent the image sensor and an illumination source comprising coherent light or partially coherent light. The source illuminates the sample through at least one aperture, fiber-optic cable or optical waveguide, based on the lens-free imaging concept. The system illuminates the sample through a plurality of different angles. In order to achieve this illumination in different angles, the light source is rotated. A portable tomographic imager is also described. It is based on the same lens-free imaging principle. Instead of rotating a single light source, a plurality of light sources is used.

Also, United States patent application US2015204773A1 discloses a system for three dimensional imaging of motile objects, such as sperm, based on an image sensor and a sample holder adjacent to the image sensor. In this system, two illumination sources are used, each one illuminating at a different wavelength.

Both the system disclosed in WO2012/094523A2 and the one disclosed in US2015204773A1 imply 'off-line' measurement methodologies (sample analysis in the laboratory). The sample is confined within a sample holder or chamber and the imaging technique is applied. These approaches are not suitable for online measurements, where especial mechanical parts are needed for allowing a continuous flow through the detection cell. Additionally, these solutions rely on algorithms with a huge computational need for reconstructing the images, which may jeopardize their application in systems where a high throughput and real time response is needed, for example when measuring running fluids.

However, as already explained, industrial machines require an analysis on their condition in real time. Therefore, there is a need for developing new systems for oil inspection in real time and with as much sample volume as possible, overcoming the cited drawbacks.

DESCRIPTION OF THE INVENTION

The present invention attempts to resolve the drawbacks mentioned above by means of a system for inspecting oil with reduced size and number of components with respect to conventional ones. The reduction in size improves its portability and its capacity to be implemented in many more types of industrial machines, including inside other larger components, like filters or pumps. Its reduction in number of components reduces the risk of failure, increases its lifetime and eases the assembly. Additionally, it is remarkable that the current invention is able to improve the inspection area and the optical performance (contrast and spatial aberrations) while keeping the same detector size. This contribution is the key for increasing the sample volume inspected by the sensor.

In a first aspect of the present invention, it is provided a sensor system for inspecting oil, which comprises a micromechanical cell defining a cavity, the micromechanical cell being configured for allowing the entrance of oil within said cavity and the outcome of oil from said cavity through respective inlet and outlet. The sensor system comprises inside said micromechanical cell: a first transparent protective means configured to isolate the inner part of said first member from said cavity to be occupied with oil; a second transparent protective means configured to isolate the inner part of said second member from said cavity to be occupied with oil; a light source disposed in said first member and configured to emit incoherent light towards said oil disposed within said cavity; an opaque plate disposed between said light source and said first transparent protective means, said plate having a pin-hole configured to permit the passage of illumination towards said cavity to be occupied with oil, said pin-hole being located at a first distance from a focussing plane defined by said cavity; an image sensor disposed in said second member situated on the opposite side of the cavity with respect to said first member and configured to capture a sequence of images of the oil disposed within said cavity, said image sensor being located at a second distance from said focussing plane defined by said cavity.

In a particular embodiment, the system further comprises a diffuser disposed between said light source and said plate defining the pin-hole, said diffuser being configured to provide homogeneous lighting to said cavity.

In a particular embodiment, the system further comprises processing means configured to process said sequence of images and to determine the presence of particles and bubbles and a degradation value of the oil.

In a particular embodiment, the light source comprises on one or more LED diodes.

In a particular embodiment, the image sensor comprises a CMOS sensor or a CCD camera.

In a particular embodiment, the pin-hole has a diameter varying in the range of 30 μm to about 300 μm. Said diameter preferably varies in the range of 50 μm to about 150 μm.

In a particular embodiment, the first distance at which said pin-hole is located from said focussing plane is in the range of 10 mm to about 30 mm. Said distance preferably varies in the range of 15 mm to about 25 mm.

In a particular embodiment, the distance at which said image sensor is located from said focussing plane is in between 1 and 3 mm. The distance preferably varies between 1 and 2 mm.

In a particular embodiment, the oil is static within said cavity. Alternatively, the oil is in motion within said cavity.

In a particular embodiment, the micromechanical cell comprises a first member and a second member defining said cavity therebetween.

In a particular embodiment, the inlet and outlet are inclined with respect to said cavity, thus minimizing the separation between the oil located within said cavity and said image sensor.

Additional advantages and features of the invention will become apparent from the detail description that follows and will be particularly pointed out in the appended claims.

BRIEF DESCRIPTION OF THE DRAWINGS

To complete the description and in order to provide for a better understanding of the invention, a set of drawings is provided. Said drawings form an integral part of the description and illustrate an embodiment of the invention, which should not be interpreted as restricting the scope of the invention, but just as an example of how the invention can be carried out. The drawings comprise the following figures.

DESCRIPTION OF AN EMBODIMENT OF THE INVENTION

Figure 1:
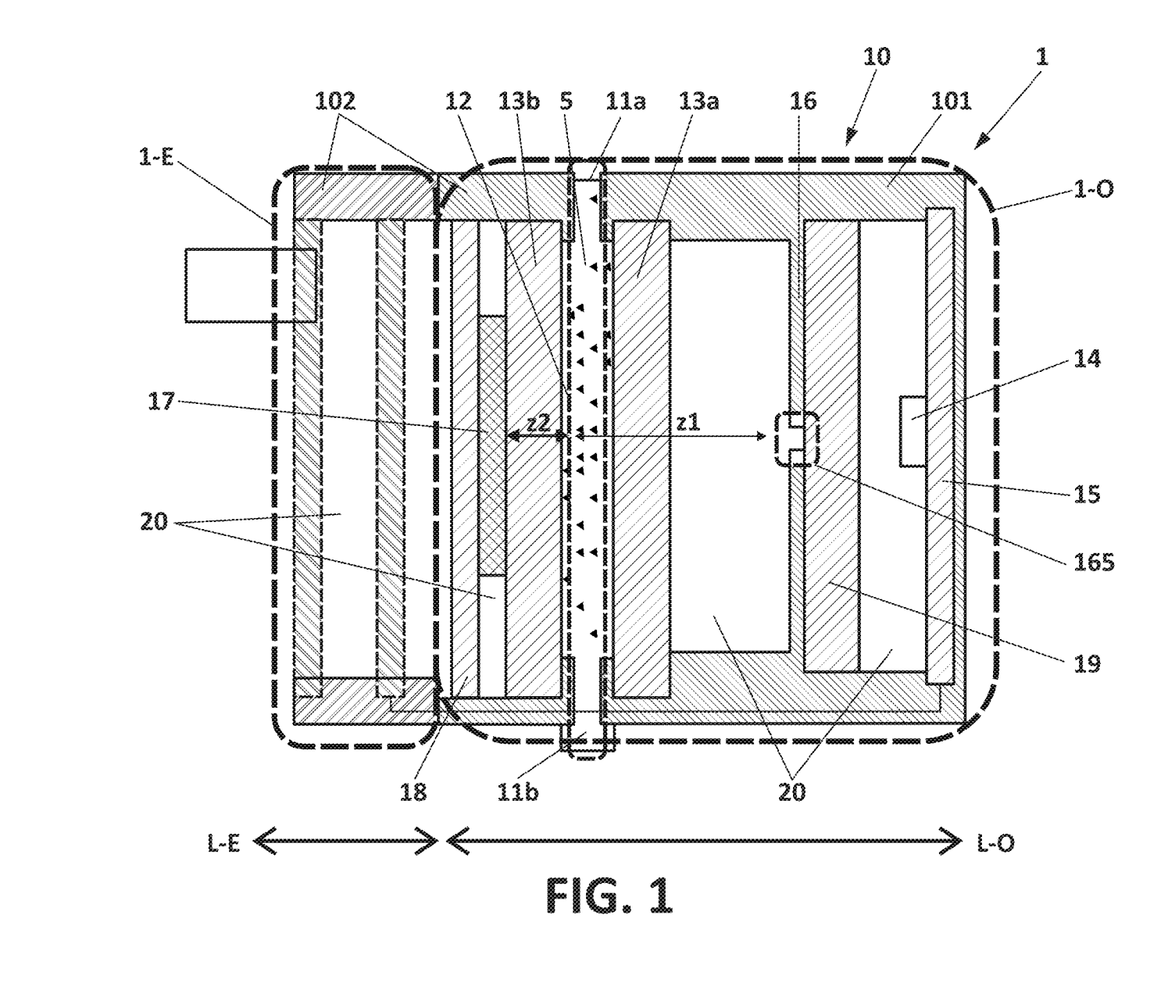
FIG. 1 shows an outline of a sensor system according to a possible embodiment of the invention.

FIG. 1 represents a scheme of a sensor system 1 for inspecting a fluid, of the invention. The fluid may include undesired particles and/or undesired bubbles. The fluid is inspected in order to determine the amount, nature and size of these particles and/or bubbles. This sensor system 1 has been conceived as an autonomous system with totally independent functioning, which delivers auto interpretable measurements, calibrated and corrected for the entire defined operating range.

The sensor system is based on lens-free imaging. The sensor system 1 comprises an optical part 1-O and an electronic part 1-E (or video acquisition and processing sub-system). The electronic part 1-E, schematically represented in FIG. 1 on the left, is a conventional one. In a preferred embodiment, it is similar to the one described in WO2014/154915A1. FIG. 1 illustrates a fluid 5 to be imaged that is disposed in a cavity, space or area 12 between a light source 14 and an image sensor 17.

Figure 2A:
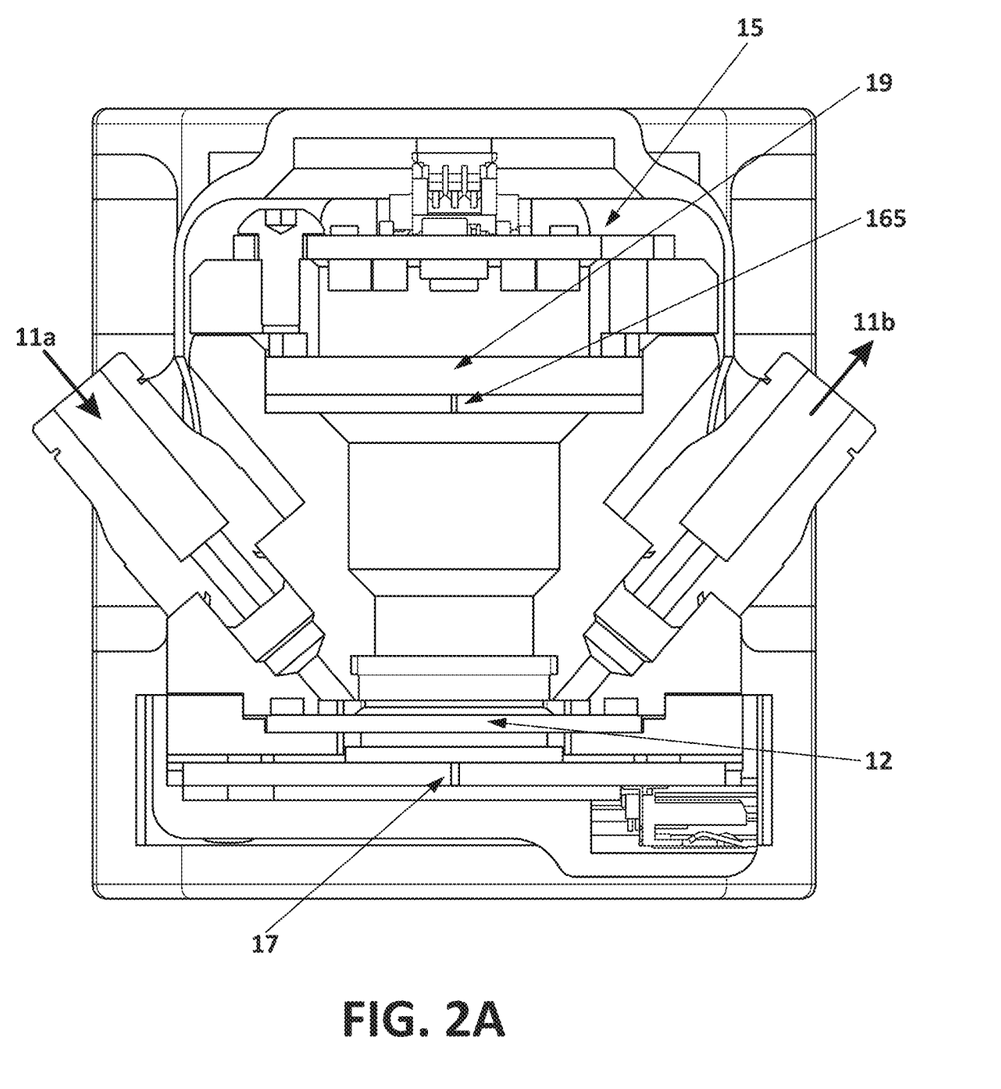
FIG. 2A shows a sensor system according to another embodiment of the invention. This configuration has inclined inlet/outlet points.
Figure 2B:
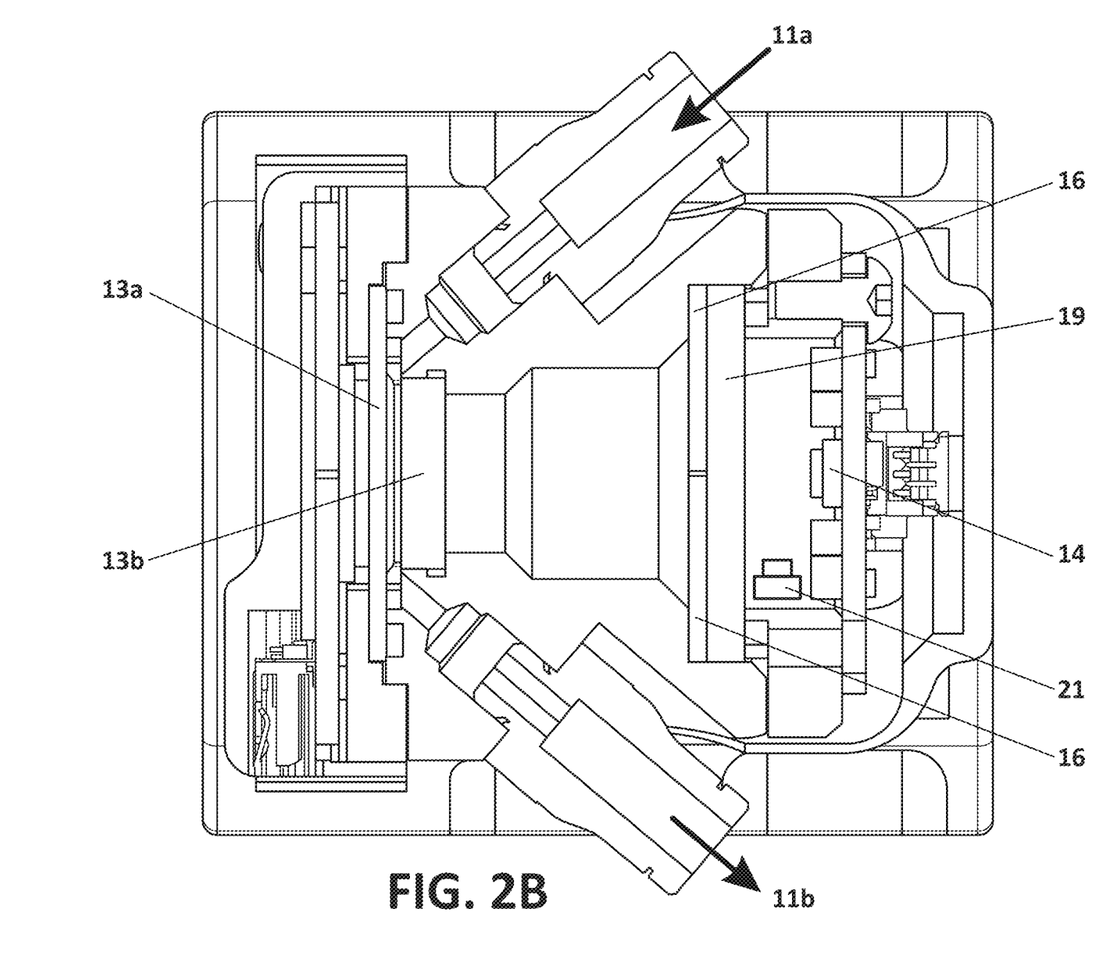
FIG. 2B shows an outline of the sensor system of FIG. 2A.

As described below, the sensor system 1 operates on a micromechanical cell 10 through which the fluid 5 under supervision circulates. In a preferred embodiment, this fluid is oil, more preferably lubricating oil. The fluid 5 is either static or in motion (circulating fluid) and accesses the area under supervision (supervision cavity, area or space 12) through two inlet/outlet points 11a 11b. In other words, the fluid 5 under supervision is supervised when it fills a supervision area 12 disposed within micromechanical cell 10. Inlet/outlet points 11a 11b are not necessarily parallel to the cavity 12 in which fluid 5 is supervised. They can alternatively be inclined with respect to this area 12. In fact, a configuration having inclined inlet/outlet points 11a 11b, as shown in FIGS. 2A and 2B, contributes to reduce the separation between the sample and the image sensor (not yet described).

Two members 101 102 form the micromechanical cell 10 which defines therebetween a cavity, space or area 12 in fluid contact with input portion 11a and output portion 11b. Space 12 is separated from the remainder of the interior of micromechanical cell 10 (defined by members 101 102) by transparent protective means 13a 13b. In this context, "transparent" means "transparent in the wavelength operated by light source 14", not yet described, that Is to say, the transparent protective means 13a 13b allow light to pass through them. The protective means 13a 13b, also referred to as protective windows, are made of any suitable transparent material. Non-limiting examples of suitable transparent materials are plastics, such as PMMA or polystyrene (PS), or glass, such as borosilicate, quartz or sapphire. These transparent windows 13a 13b seal the cavity or space 12 occupied by the fluid 5 under supervision. These windows 13a 13b act as a seal so that the fluid does not leak towards the optical equipment housed within the micromechanical cell 10. In other words, the fluid passes through (or statically fills) space or area 12 and the fluid is "transversally" inspected and measured. Getting rid of the focusing lens mitigates the problems related with the assembly tolerance dependent optical magnifications. Therefore, the proposed system can work without an optical autocalibration. However, if even more accurate size measurements are needed, the seals or windows 13a and/or 13b may be marked with precision patterns to calibrate every single measurement, as described by the inventors in WO2014/154915A1.

The optical part 1-O of the sensor system 1 comprises a light source 14 configured to emit light, in such a way that the fluid 5 (or flow of fluid) which fills cavity or space 12 is subjected to a beam of light. In the scheme of FIG. 1, the light source 14 is embedded or integrated within a board, such as a PCB (printed circuit board) 15. The light source 14 has light modulation capabilities in terms of light power and light pulse duration. In a preferred embodiment, light source 14 is a source of incoherent light. In other words, the light source 14 preferably supplies a beam of white light to the fluid 5. In a particular embodiment, light source 14 comprises on one or more LED diodes (Light Emitting Diodes) which continuously light the flow 5 which circulates through or fills cavity or space 12 between members 101 102. A diffuser or frosted window 19 may be disposed in front of light source 14. The diffuser 19 is discussed in detail later. In other words, in this embodiment the light source is a LED emitter. Preferably, the light emitting system has a control system (closed loop control) of the polarisation of the LED emitter based on changes in temperature which prevent fluctuations in emission due to said changes in temperature.

As a person skilled in the art knows, when the temperature rises there is a reduction in the emission of the LEDs due to a decrease in the efficiency of the photons. By means of this control, if the temperature rises the power is increased so that the apparent emitted light remains constant. In a possible embodiment, the light source 14 also comprises a photodiode 21 near the lighting zone to calculate the error of that closed loop. An embedded processor, not specifically shown, but for example integrated within PCB 15, preferably controls the light source 14 through LED control signals and compensation data. In an alternative embodiment, light source 14 is a conventional light bulb or a Xenon lamp with a filter. In fact, any source of incoherent light could be used (for example a broadband extended source). The light source 14 preferably has a spectral bandwidth that is between 400 and about 700 nm, although the spectral bandwidth may be even smaller or larger.

Opposite the light source 14, on the other side of the cavity, space or area 12 through which the flow 5 circulates (or simply, the cavity, space or area 12 filled with fluid 5), an image sensor or image capture system 17 is placed. The light emitted by the light source 14 that is not absorbed by the fluid 5 is gathered by means of a detector (for example, a photodiode or photodiode array). In an inspection system implementing artificial vision, as is the case of the sensor system 1, back lighting is used, which means that the optical receiver element (i.e. photodiode array) collects the light that passes through the flow of fluid 5. In the scheme of FIG. 1, the image sensor 17 is embedded or integrated within a board, such as a PCB (printed circuit board) 18. The image sensor 17 is configured to capture a video sequence (i.e. a train of images) of the zone of interest 12 in the passage of the fluid (preferably oil). This image capture is carried out with a defined spatial resolution and maintaining a general criterion of reduced size and low cost. In other words, the "defined spatial resolution" refers to the fact that the image sensor 17 is capable of determining a defined minimum size of particle, which is in the region of 4 microns over an inspection cavity or area 12 of about 100 mm$^2$. This resolution is achieved by optimising several conditions, such as the area to be inspected, the size of the image sensor 17 and its number of pixels. It is remarked that the system 1 must have a small size and be as compact as possible.

In a preferred embodiment, the image sensor or image capture system 17 is a camera, more preferably a camera based on complementary metal-oxide semiconductor (CMOS) sensor or CMOS detector (the CMOS sensor is the camera component that receives the image). Therefore, a CMOS camera has a 2D array of photoreceptors manufactured with CMOS technology. For this reason, occasionally in this text the expression "CMOS sensor" or "CMOS detector" is used to refer to the image sensor 17. Alternatively, the image sensor 17 may include, for example, a charged coupled device (CCD) camera. The image sensor 17 may be monochromatic or colour. The image sensor 17 has a small pixel size and therefore produces higher resolutions. In a particular embodiment, the pixel size of the image sensor 17 is less than 10.0 µm in size and preferably smaller than 6.0 µm (for example, 2.0 µm or smaller). In a possible embodiment, an acquisition and processing system of 15 frames per second (15 FPS) is used. For example, and Omnivision detector can be used with a 14 megapixel camera. With this image sensor 17 a spatial resolution better than pixel size is obtained. It is remarkable that the proposed invention is able to use an inspection area larger than a lens-based system at the same object-detector-light component placing distances.

Figure 3:
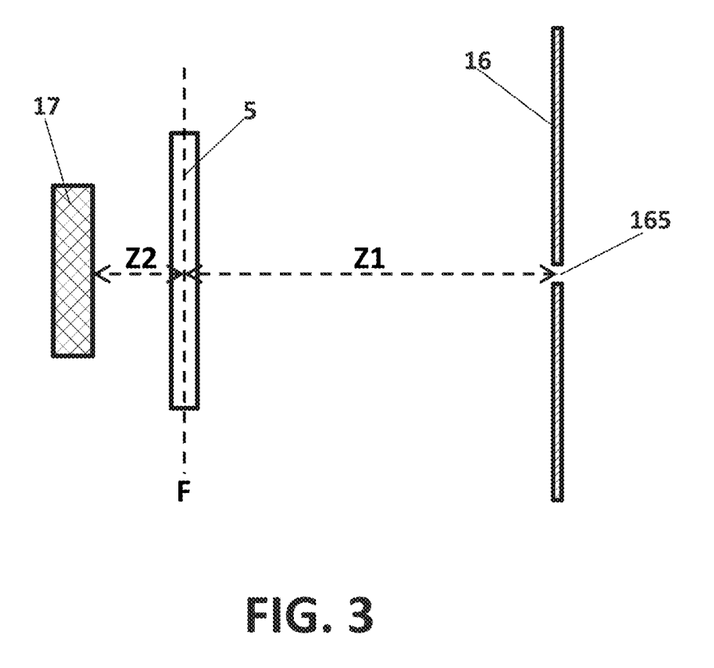
FIG. 3 shows in detail the image sensor, the focussing plane, the pin-hole and the distances between image sensor and focussing plane and between focussing plane and pin-hole.

The minimum size of particle that it must be possible to discriminate is of approximately 4 µm. The area to be captured in each image by the image sensor 17 must be such that it is capable of capturing particles of 4 µm and more. In a preferred embodiment, the area to be captured is of several square millimetres. In one example, said area to be captured is of 100 mm². The distance z2 between the object (focussing plane or plane of passage of the fluid under inspection) and the image sensor 17 is desirably as minimum as possible and does not exceed approximately 5 mm, so that the system 1 is remarkably compact and small. Distance z2 is selected to be above 1 mm, in order to leave room to place transparent protective means 13b, which is necessary in order to prevent fluid from leaking into the inner cavity of member 102. In particular, distance z2 is preferably between 1 and 3 mm and more preferably between 1 and 2 mm approximately. The outline represented in FIG. 3 shows in detail the image sensor 17, the focussing plane F located at the fluid 5 under supervision and distance z2.

The images (for example video sequence) captured by this camera are processed in an embedded processor of the electronics part 1-E (for example integrated within PCB 18). In a preferred embodiment, the not shown embedded processor is a DSP device (Digital Signal Processor). This embedded processor is the one that analyses for each image whether there are bubbles and particles and counts them. In other words, the processor is responsible for extracting the image from the CMOS and processing it. To do this, it has an intermediate memory for subsequent processing. In a possible embodiment, this intermediate memory is a DDR2 external memory. In FIG. 1, the electronic part 1-E comprises, in addition to the embedded processor and memory means, auxiliary systems such as communication interface, power source, memory, temperature sensor, among others. Also, there is a software part, formed by the group of algorithms in charge of the detection and classification of particles, bubble detection and determination of degradation. Details on the video acquisition, processing of images and counting of bubbles and particles are out of the present invention. This acquisition and processing is preferably similar to the one described in detail in WO2014/154915A1. In a particular embodiment, in which more accuracy is required, the acquisition and processing unit is responsible for applying algorithms for the dimensional calibration of the measurement. Basically, the auto-calibration is based on identifying using the image sensor 17 markings, of a known size, made on windows 13a and/or 13b, which also work as calibration windows, so that any identified image can then be scaled. Machine vision algorithms are used, which directly use the image captured by the image sensor, rather than requiring a reconstruction of the image or a pre-processing of the image using holographic techniques. This auto-calibration makes it possible to diminish the effects of the mechanical and assembly tolerance on the size of the images of particles captured on the camera. The auto-calibration allows, in contrast to conventional oil supervision systems, automatic compensation of these differences in the sizes of the objects captured due to the manufacturing and assembly dispersion. It also means that it is not necessary to dimensionally calibrate each unit of equipment. Also, it makes the system more robust against potential degradations occurring in the machine. In other words, the auto-calibration algorithms impose the required precision of the system on the auto-calibration markings and not on the entire micromechanical system, although in practice the result is equivalent to imposing said precision requirements on the whole system.

Between the light source 14 and the protective means 13a (the protective means closest to the light source or, in other words, the protective means that separates member 101 from the supervision cavity, area or space 12), there is a sheet, plate or spatial filter 16. The sheet or plate 16 is opaque. In the context of the present invention, "opaque" means "opaque in the wavelength operated by light source 14". The sheet, plate or spatial filter 16 can be made of any material, such as plastic or metal. The sheet or plate 16 has an aperture or pin-hole 165 contained therein that is configured to permit the passage of illumination (e.g., spatial aperture or pin-hole). The pin-hole 165 can have any section. In a particular embodiment, it has been implemented with circular section. The pin-hole 165 has a diameter that is typically in the range of 30 µm to about 300 µm. More preferably, it varies in the range of 50 µm to about 150 µm. The smaller the hole is, the more is improved the beam quality, but the more is reduced the power. If, on the contrary, a too large hole is selected, the beam quality may not be improved as much as desired.

Thanks to the use of the aperture or pin-hole 165, there is no need to use a lens for transporting the image from the object (the fluid 5) to the image sensor 17, as was required in conventional sensing systems. In other words, thanks to the pin-hole 165, the image sensor (camera) 17 is capable of appropriately focusing the object. The diameter of the pin-hole 165 also affects in the depth of field, but with the proposed diameters, the current invention is able to offer a larger depth of field than a lens-based solution. It is remarked that avoiding the use of a lens, which in this application was normally a macro-lens, saves a great deal of space in the sensor system 1 while keeps even a larger sampling volume and image quality. A reduction in size, an increase in compactness and an improvement in sampling volume and image quality across all that volume is therefore achieved.

As seen in FIG. 1, the aperture or pin-hole 165 is located at a distance z1 from the focusing plane or plane of passage of the fluid under inspection (plane of the area or space 12 occupied by the fluid 5 under supervision). Distance z1 between the object (focusing plane or plane of passage of the fluid under inspection) and the pin-hole 165 is desirably as minimum as possible, because it enables a reduction in the size of the cell 10. The outline represented in FIG. 3 shows in detail the pin-hole 165, the focussing plane F located at the fluid 5 under supervision and distance z1. In a particular embodiment, distance z1 is in the range of 10 mm to about 30 mm. More preferably, it varies in the range of 15 mm to about 25 mm.

The values of z1, z2 and diameter of pin-hole $D_{ph}$ may vary depending on the application for which the sensor system is used. In general, the larger the diameter of the pin-hole $D_{ph}$, the less light power will be needed, but the larger z1 is required and the smaller z2 is achieved. On the contrary, reducing the diameter of the pin-hole $D_{ph}$, will require increasing the light power applied, but a smaller z1 and a larger z2 could be reached, allowing a thicker protection glass between the sample and the detector and enabling a much more compact complete system. As an approximation, the following relation may be used:

$$\text{Minimum object Diameter in detector} = \text{pin-hole Diameter} * z2/z1$$

The selection of these values also depends on the fluid under supervision. For example, if the fluid is static, a pin-hole with smaller diameter can be chosen, because although less amount of light goes through the pin-hole, the shutter of the image sensor (camera) 17 can remain open for a longer time without risking the quality of the image taken (because the fluid does not substantially move). On the contrary, if the fluid is in motion, the higher its velocity, the larger the diameter of the pin-hole must be, in order to let more light go through the pin-hole, thus minimizing the time required for the image sensor shutter to be open to capture the image. Additionally, the amount of light permitted to go through the diameter of the pin-hole can be compensated with an increase in power in the light source.

In a preferred embodiment, between the light source 14 and the fluid 5 under supervision, a diffuser 19 is placed. In particular, the diffuser 19 is located between the light source 14 and the sheet, plate or spatial filter 16 defining the pin-hole 165. Still more preferably, the diffuser 19 is placed adjacent to sheet, plate or spatial filter 16. The principal mission of diffuser 19 is diffusing the amount of light emitted by the light source 14 in order to obtain a homogenous lighting over the entire cavity or area 12 (amount of fluid 5) that is being inspected. In other words, diffuser 19 increases the incoherence of the light emitted by the light source 14. The diffuser 19 is made of a transparent material that allows light through it. Therefore, the light source 14 can light the fluid 5 appropriately, and by means of the detection system (image system 17) it is possible to visualise the illuminated zone and to capture the image of the fluid. In a preferred embodiment, the diffuser 19 is made of glass, for example a frosted glass. Thanks to this diffuser 19 it is possible to light the area under inspection still in a more homogeneous manner. It has been observed that this is important in order to obtain reliable results (optimal particle detection). As shown in the embodiment represented in FIG. 1, it is desirable to leave a certain distance dl between the board (for example PCB) 15 and the closest surface of diffuser 19 in order not to heat diffuser 19 above a certain temperature. Taking into account the typical values of power of the light source 14, it has been experimentally observed that distance dl may be in the range of about 1 mm to about 5 mm. More preferably, it may be in the range of about 1 mm to about 3 mm (for example 2 mm). The space within the micromechanical cell 10 which is not occupied by any component is occupied with open air. This space is referred to as 20 in FIG. 1.

In sum, the proposed sensor system 1 is very compact and of reduced size. A prototype has been developed having a total length of 45 mm approximately. This length includes the length L-O of the optical part 1-O and the length L-E of the electrical part 1-E, wherein L-O=31 mm approximately and L-E=14 mm approx. The width of the sensor system 1 is 20 mm approx. Its height is 23 mm approx.

Figure 4:
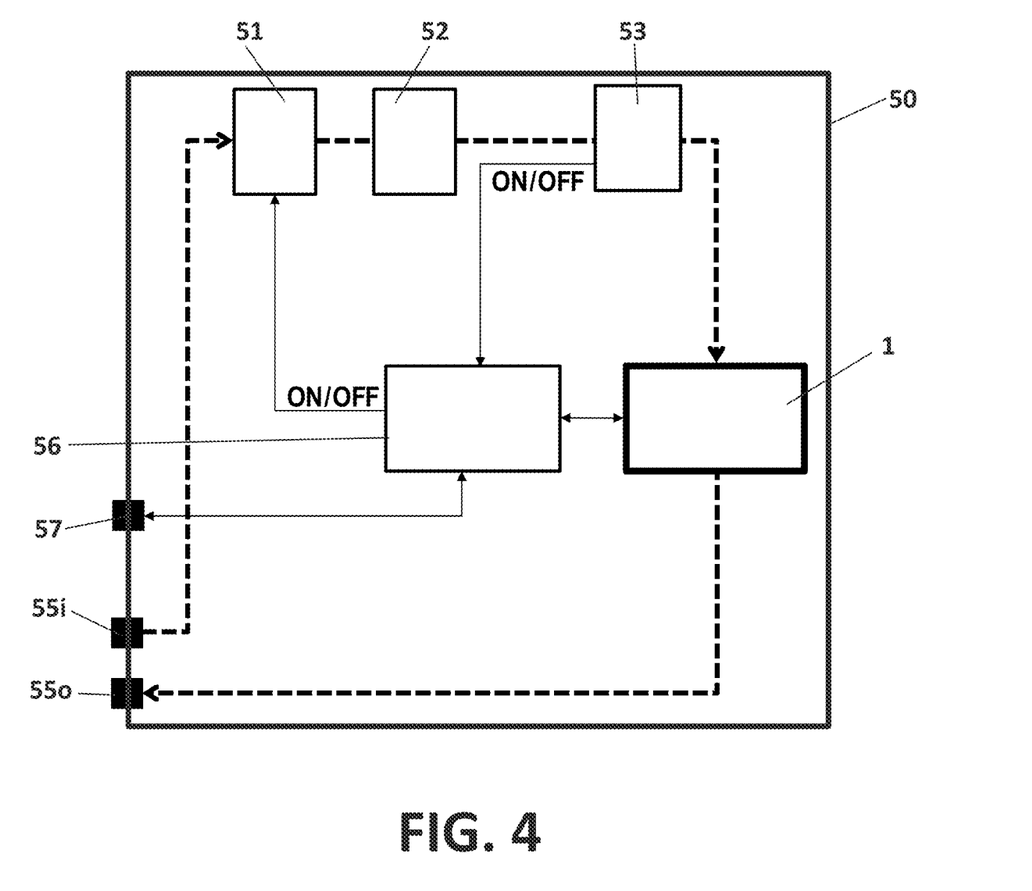
FIG. 4 represents a general outline of a monitoring system, including the sensor system of the invention.

FIG. 4 represents a general outline of a monitoring or inspection system in which the sensor system 1 of FIGS. 1 and 2A-2B can be included. Apart from the sensor system 1 already described, the complete system is composed of a series of sub-systems connected to each other and contained within a receptacle or container 50. This monitoring or inspection system is similar to the one described in WO2014/154915A1. The sub-systems are as follows:

A hydraulic conditioning sub-system, made up of components for flow control 52, oil flow control by means of electrovalve 51, pressure control 53, safety filter 54 and the inlet 55*i* and outlet 55*o* piping. The reading and operation of the active hydraulic elements is carried out from an electronic sub-system 56. It is noteworthy that the hydraulic conditioning sub-system does not include any pump. In a preferred embodiment, the system of the invention is designed to be installed in a by-pass of the lubricating system of certain machinery. The installation takes advantage of the pressure differences for the fluid to circulate to the measurement module 1 (sensor system) where the oil inspection will take place.

The electronic sub-system 56 is formed by an embedded electronic platform for managing all active sub-systems and managing data channels. This embedded electronic platform performs the global management of information and control of the hydraulic and measurement sub-systems. This sub-system is considered to include the internal and external connection technologies and the power system 57.

The container and fastening system 50 incorporates the external hydraulic and electrical connections and the fastening system (not shown in FIG. 4) to the installation's place of destination. The system 50 is specifically designed for its direct integration into the lubricating systems of machinery but without affecting the operating conditions thereof. This is achieved by means of the hydraulic sub-systems of the sensor which make it possible to carry out controlled sampling with low content in lubricating oil. The container and the fastening system 50 houses and integrates the different elements in an appropriate manner and allows external communication for the intake and output of the fluid, through the respective inlet 55*i* and outlet 55*o* (as the measurement is carried out in the measurement sub-system 1) and provides the communication interfaces and power supply 57 in order to be able to carry the sensor's results to the machine in question or wherever required.

The hydraulic sub-systems in turn allow the fluid to be measured to be conditioned, thereby reducing the effects of external conditions or factors on the end result. The system has also been developed to avoid the influence of environmental factors such as changes in temperature. In this sense, the sensor system has temperature measurers that actuate the intensity of the light emitting diode and thereby prevent differences in emission related to changes in temperature.

As can be seen from FIG. 4, the fluid enters the container 50 through the inlet 55*i*. The flow of fluid follows the direction of the dotted arrow line. The fluid circulates through the inside of the container 50 through appropriate channelling means, such as pipes. Through the inlet and outlet fittings and the sub-systems it is possible to carry out a representative sampling of the fluid (for example, oil) and to condition it to obtain representative measurements of its real condition.

Flow control 52 makes it possible for the system to obtain a fixed flow which makes it possible to know the amount of fluid that is being measured and thereby to obtain the particle concentration therein. In other words, the flow control 52 makes it possible to give values of, for example 100 particles per millilitre. Otherwise, it would only be possible to say that 100 particles were detected, in absolute terms.

The pressure switch 53 is a pressure system that ensures that there is pressure in the system and therefore guarantees that there is a flow of the fluid (for example, of oil). Therefore, it is a pressure switch designed to identify low pressures. The issue is that the machines in which the sensor system 1 is installed are not functioning continuously, and when they are stopped there is no oil pressure, meaning that there is no entry of oil in the sensor system, which results in the measurement eventually taken not being representative, because oil is not being measured. With the pressure switch 53 there is detection of pressure when there is and when there isn't pressure, in order to validate a taken measurement and thereby ensure that it is oil and not air that is being measured.

The inlet electrovalve 51 performs the function of allowing the oil in or not. When the electrovalve is "ON", the system is open for the oil to pass; and when the electrovalve is "OFF", the system is closed and the oil does not enter. This is carried out so that the oil is not continuously flowing through the system, for two important reasons: (1) to carry out controlled sampling and interfere as little as possible with the machine's lubricating systems; (2) to ensure that the hydraulic sub-systems are not affected by dirt that could be generated by the continuous flow of oil.

The ON/OFF arrows indicate in respect of the components next to which they appear in FIG. 4, that these components are controlled electronically. Specifically, on electrovalve 51 the ON/OFF arrow indicates the opening and closing off of entry to the oil; and in the pressure switch 53 the ON/OFF arrow provide an indication of the pressure level in the system. The pressure switch 53 is "ON" when a specific pressure value is exceeded and then it is assumed that oil has entered.

Next some experiments are explained. They have been monitored by establishing a USB connection between board 18 and a computer.

Experiment 1

The goal of this experiment is to illustrate the general performance of the system shown in FIGS. 2A-2B in terms of its ability to generate a useful image of the fluid sample for its later processing. The fluid sample used is lube oil contaminated with wear debris and air and water bubbles.

Figure 5:
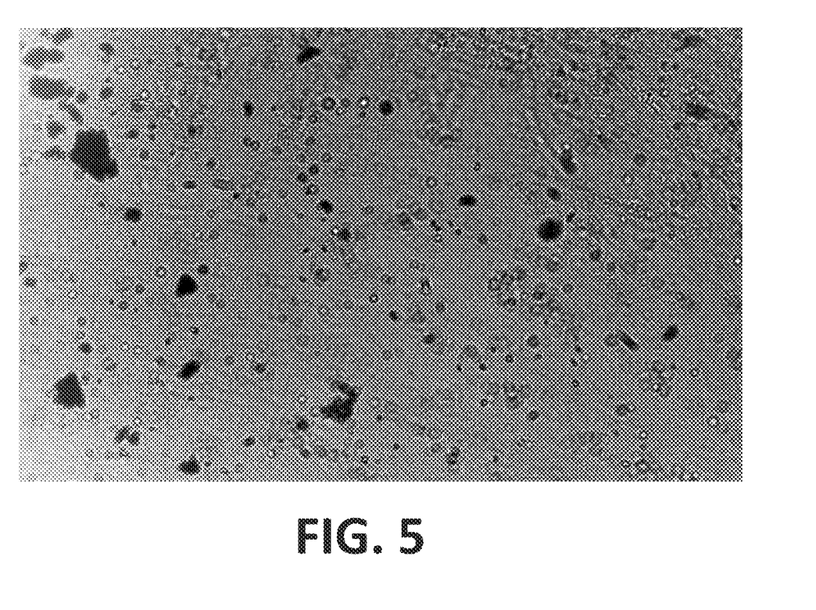
FIG. 5 shows an image captured in a first experiment of the inventive sensor system.

FIG. 5 represents an image captured in this experiment using a prototype according to FIGS. 2A-2B. The light source was a white LED having beam aperture of 60°. The plate defining the pin-hole was placed at a distance 1 mm from the LED. The diameter of the pin-hole was 150 µm. A diffuser of 3 mm thickness was placed adjacent to the plate. In the prototype, lube oil was isolated from the sensor system by two protective windows of 1 mm thickness made of quartz. Lube oil was fed into that cavity with an auxiliary hydraulic pump at a flow rate of 0.5 L/minute. Distance z1 from the cavity to the pinhole was selected to be 19 mm. The image sensor was a CMOS sensor of 5 Megapixel. Distance z2 from the CMOS sensor to the cavity was selected to be 2.1 mm.

As can be observed in FIG. 5, the system is able to capture a valid image of the running fluid where the wear particulates and bubbles are recognizable.

Experiment 2

Figure 6:
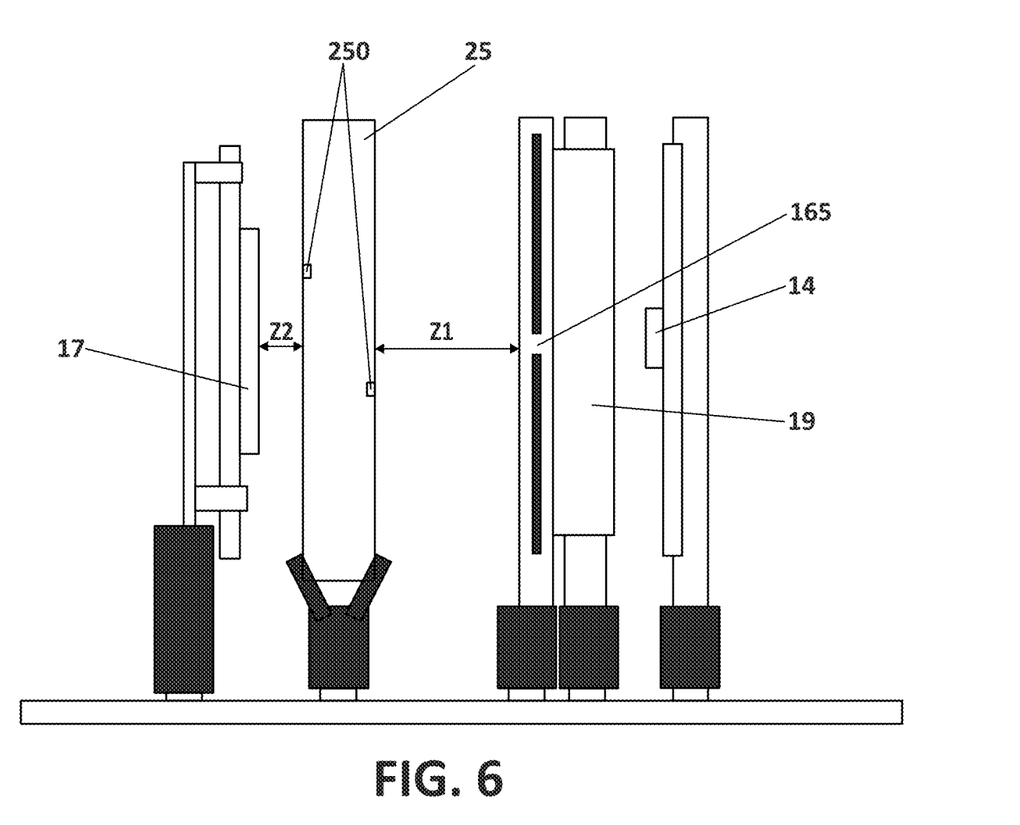
FIG. 6 shows the setup of a second experiment of the inventive sensor system.

The goal of this experiment is to illustrate the effect of the diameter of the pinhole 165 and of the z1/z2 distances in the system magnifications and depth of field. The setup of the experiment is described in the FIG. 6. The experiment setup shows a 10 Mpix CMOS imager 17, a sample object 25 located at distance z2 from the CMOS imager 17, a plate having a pinhole 165 placed at distance z1 from the object 25, a diffuser (3 mm thick/PMMA material) 19 placed immediately after the pinhole 165 and a partially incoherent light source (White LED) 14 at 1 mm from diffuser 19. The sample object 25 is a 1 mm thick quartz transparent window in which 8 circles (with diameter=200 µm) have been micromachined on its inner (4 circles) and outer surfaces (4 circles). In the outline of FIG. 6 only two circles 250 are shown.

In the experiment, different pinhole diameters are combined with different z1/z2 distances to illustrate the impact on the focusing plane and on the depth of field which becomes evident at the sharpness of the circles and their apparent diameter in the captured image. In particular, different configurations of pinholes (500 µm, 200 µm and 50 µm) have been used, in order to observe the behavior of each of them. For each pinhole configuration, different values of distances z1 and z2 have been tried. First, the sample object 25 has been located close to the CMOS imager 17 (z2=0) and the optimal value of z1 has been determined, in terms of achieving best focus. Once z1 is determined, the light source 14 and the pinhole 165 are placed. Next, the position of the sample object 25 is modified, thus obtaining new values for z1 and z2. In each position a capture of the image is taken. Based on the formula:

Minimum object Diameter in detector=pin-hole Diameter*$z2/z1$

We have observed that:

Given a sample object and having a certain distance z2, the bigger the diameter of the pinhole, the bigger is the distance z1 at which the sample object becomes focused.

Given each pinhole and given a sample object, if distance z2 is increased, the distance z1 at which the sample object becomes focused is also increased. This increase is linearly proportional.

Figure 7A:
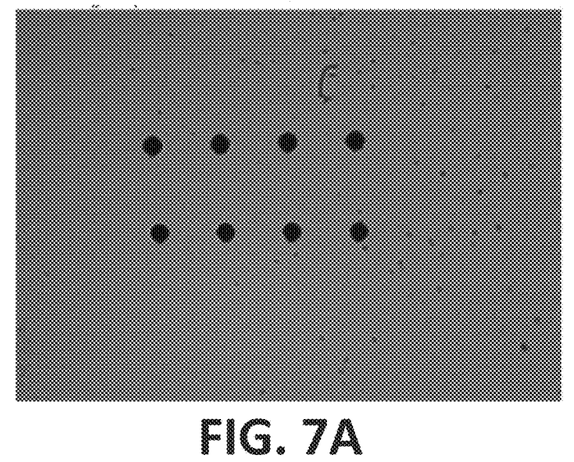
FIGS. 7A-7C show the results of a second experiment taken with diameter of pinhole=500 μm.
Figure 7B:
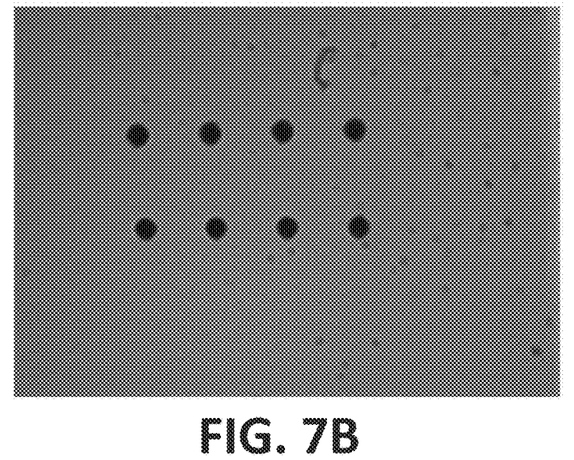
Figure 7C:
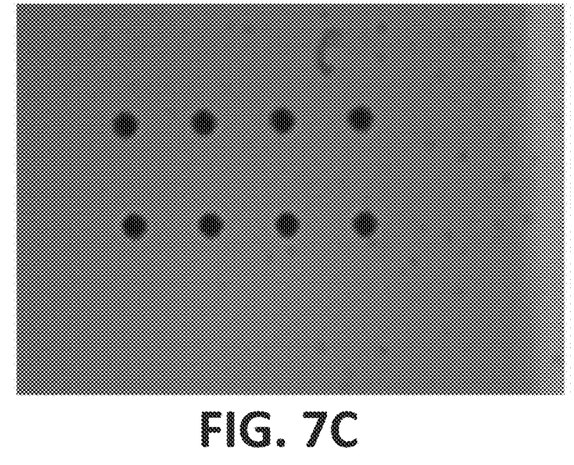

FIGS. 7A-7C show the results obtained with diameter of pinhole=500 µm. FIG. 7A shows the image taken when z2=0 mm and z1+z2=z1=35 mm (optimal focus). FIG. 7B shows the image taken when z2=2.45 mm and z1=35-2.45=32.55 mm. FIG. 7C shows the image taken when z2=4.9 mm and z1=35-4.9 mm=30.1 mm.

Figure 8A:
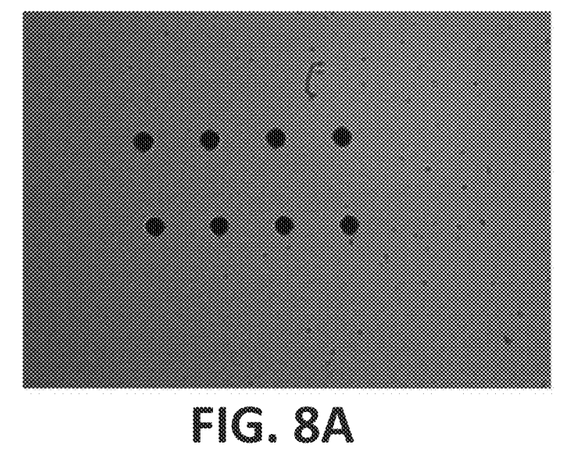
FIGS. 8A-8C show the results of the second experiment taken with diameter of pinhole=200 μm.
Figure 8B:
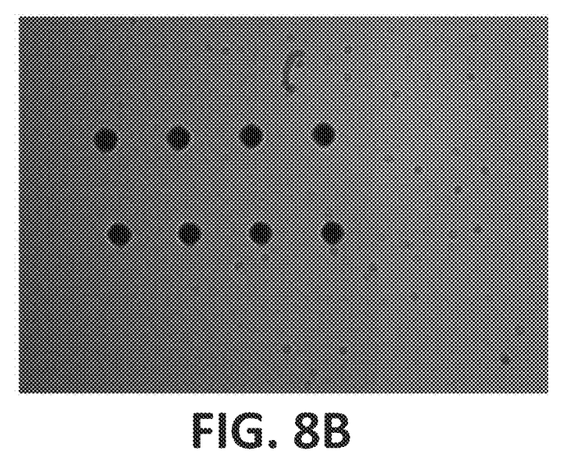
Figure 8C:
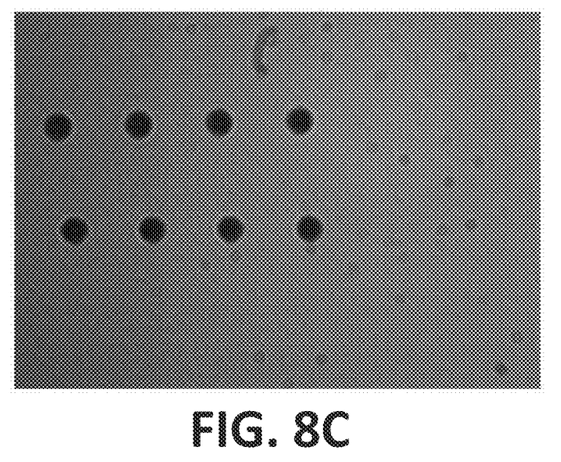

FIGS. 8A-8C show the results obtained with diameter of pinhole=200 µm. FIG. 8A shows the image taken when z2=0 mm and z1+z2=z1=28 mm (optimal focus). FIG. 7B shows the image taken when z2=2.45 mm and z1=28-2.45=25.55 mm. FIG. 7C shows the image taken when z2=4.9 mm and z1=28-4.9 mm=23.1 mm.

Figure 9A:
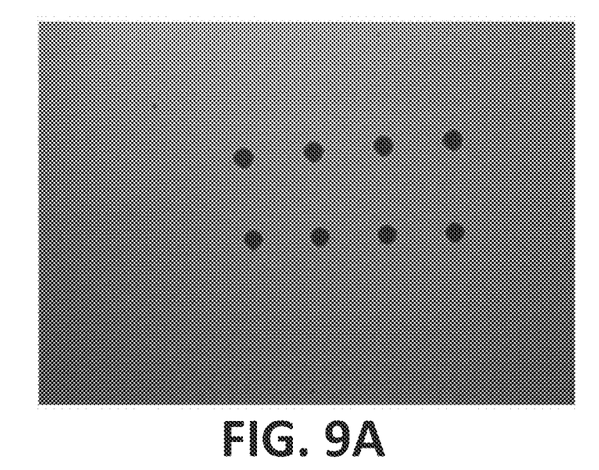
FIGS. 9A-9C show the results of the second experiment taken with diameter of pinhole=50 μm.
Figure 9B:
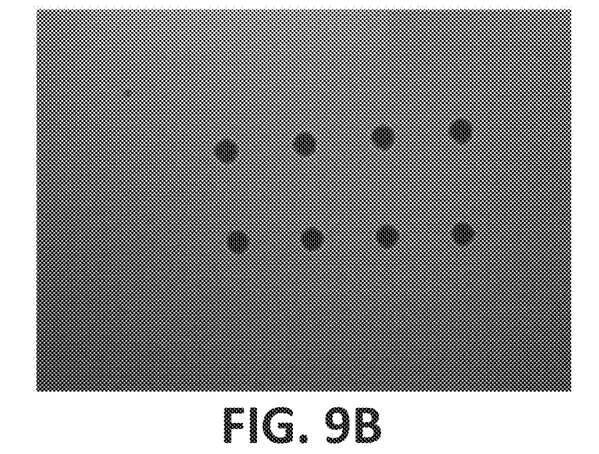
Figure 9C:
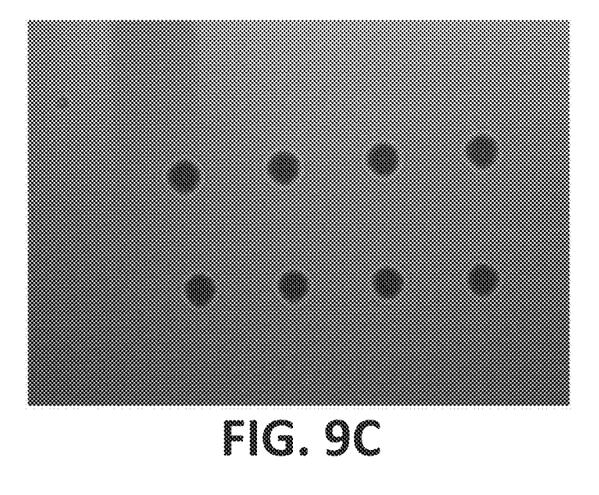

FIGS. 9A-9C show the results obtained with diameter of pinhole=50 µm. FIG. 9A shows the image taken when z2=0 mm and z1+z2=z1=15 mm (optimal focus). FIG. 9B shows the image taken when z2=2.45 mm and z1=15-2.45=12.55 mm. FIG. 9C shows the image taken when z2=4.9 mm and z1=15-4.9 mm=10.1 mm.

Figure 10A:
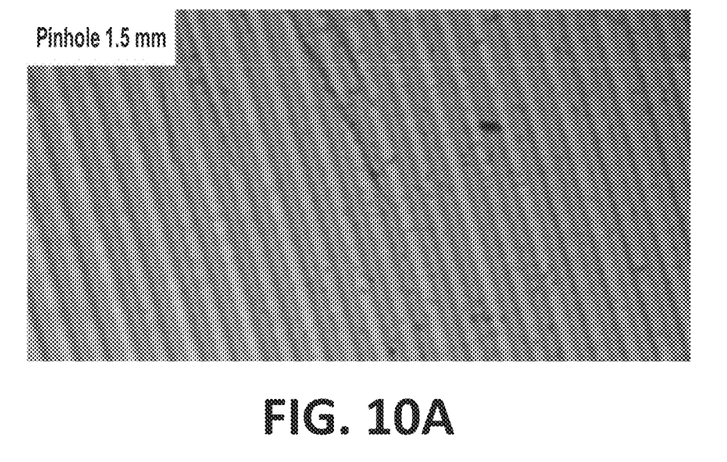
FIGS. 10A-10C represent images captured in a third experiment of the inventive sensor.
Figure 10B:
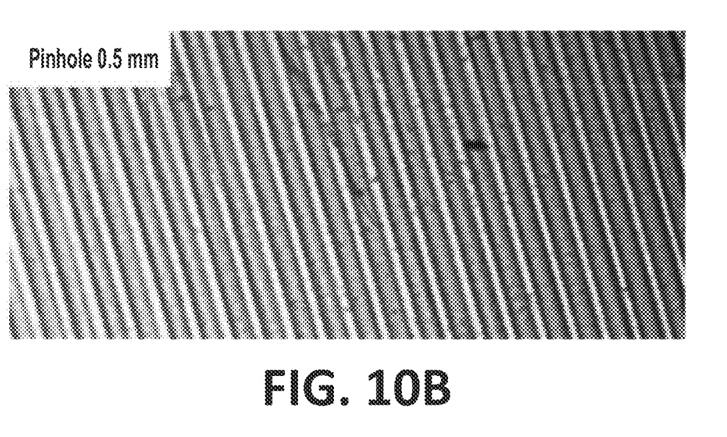
Figure 10C:
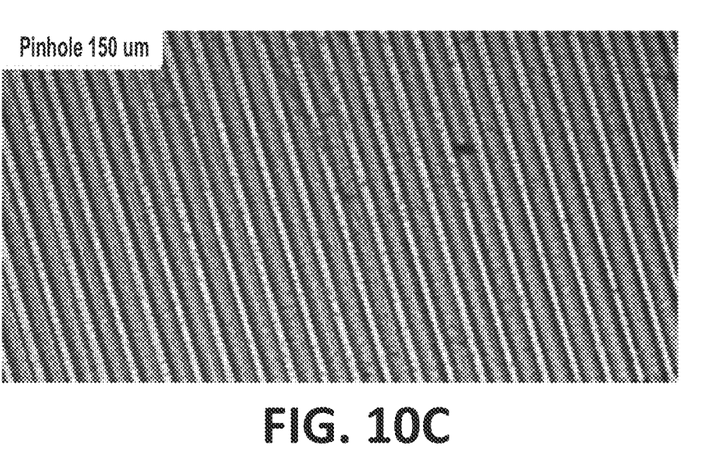

Experiment 3: The Effect of the Pinhole Diameter in the Focus Plane and Depth of Field FIGS. 10A-10C represent images captured in this experiment. For this experiment, even if the same prototype system as in Experiment 1 has been used, in this case, the lube fluid sample is replaced by a transparent solid sample with a micromachined pattern on it. The solid sample is 1 mm thick and the pattern is 100 µm deep. The pattern is faced up, therefore placed at a distance of 900 µm from the protective window inner plane. With this prototype set up, the experiment evaluates the image captured using different pin-hole diameters (1.5 mm in FIG. 10A, 0.5 mm in FIGS. 10B and 150 µm in FIG. 10C). It can be observed that the smaller the diameter of the pin-hole, the best image focusing is achieved due to the focusing plane displacement and increase in depth of field.

Throughout this document, the word "comprises" and variants thereof (such as "comprising", etc.) must not be interpreted as having an exclusive meaning, in other words, they do not exclude the possibility of what is being described incorporating other elements, steps, etc.

Finally, the invention is not limited to the specific embodiments described herein and also extends, for example, to variants that may be embodied by an average person skilled in the art (for example, with regard to the choice of materials, dimensions, components, configuration, etc.), within the scope of what is inferred from the claims.

The invention claimed is:

1. A sensor system for inspecting oil, based on lens-free imaging, which comprises a micromechanical cell defining a cavity between a first member defining a first closed area and a second member defining a second closed area, of the micromechanical cell, the micromechanical cell being configured for allowing the entrance of oil within said cavity and the outcome of oil from said cavity through respective inlet and outlet, the sensor system comprising inside said micromechanical cell:
   a first transparent protective window configured to isolate the inner part of the first closed area defined by said first member from said cavity to be occupied with oil;
   a second transparent protective window configured to isolate the inner part of the second closed area defined by said second member from said cavity to be occupied with oil;
   a light source disposed in said first member and configured to emit incoherent light towards said oil disposed within said cavity;
   an opaque plate disposed between said light source and said first transparent protective window, said opaque plate having a pin-hole configured to permit the passage of illumination towards said cavity to be occupied with oil, said pin-hole being located at a first distance from a focusing plane defined by said cavity;
   an image sensor disposed in said second member situated on the opposite side of the cavity with respect to said first member and configured to capture a sequence of images of the oil disposed within said cavity, said image sensor comprising a 2D array of photoreceptors, said image sensor being located at a second distance from said focusing plane defined by said cavity; and
   a diffuser disposed between said light source and said opaque plate defining the pin-hole, said diffuser being disposed adjacent to the opaque plate, wherein the light from the light source travels to the cavity other than through a focusing lens with said diffuser being configured to provide homogeneous lighting to said cavity.

2. The system of claim 1, further comprising a processor configured to process said sequence of images and to determine the presence of particles and bubbles and a degradation value of the oil.

3. The system of claim 1, wherein said light source comprises on one or more LED diodes.

4. The system of claim 1, wherein said image sensor comprises a CMOS sensor or a CCD camera.

5. The system of claim 1, wherein said pin-hole has a diameter between 30 µm and about 300 µm.

6. The system of claim 5, wherein said diameter is between 50 µm and about 150 µm.

7. The system of claim 1, wherein said first distance at which said pin-hole is located from said focusing plane is in the range of 10 mm to about 30 mm.

8. The system of claim 7, wherein said first distance is in the range of 15 mm to about 25 mm.

9. The system of claim 1, wherein said second distance at which said image sensor is located from said focusing plane is in between 1 mm and 3 mm.

10. The system of claim 9, wherein said second distance is between 1 mm and 2 mm.

11. The system of claim 1, wherein said oil is static within said cavity.

12. The system of claim 1, wherein said oil is in motion within said cavity.

13. The system of claim 1, wherein said inlet and outlet are inclined with respect to said cavity, thus minimizing the separation between the oil located within said cavity and said image sensor.

14. The system of claim 1, wherein said light source is embedded within a board and the distance between said board in which the light source is embedded and said diffuser is in the range of 1 mm to 5 mm.

* * * * *